United States Patent [19]
Yock

[11] Patent Number: 5,313,949
[45] Date of Patent: May 24, 1994

[54] METHOD AND APPARATUS FOR INTRAVASCULAR TWO-DIMENSIONAL ULTRASONOGRAPHY

[75] Inventor: Paul G. Yock, San Francisco, Calif.

[73] Assignee: Cardiovascular Imaging Systems Incorporated, Sunnyvale, Calif.

[21] Appl. No.: 14,906

[22] Filed: Feb. 1, 1993

Related U.S. Application Data

[63] Continuation of Ser. No. 826,260, Jan. 24, 1992, which is a continuation of Ser. No. 649,048, Feb. 1, 1991, abandoned, which is a continuation of Ser. No. 290,533, Dec. 23, 1988, Pat. No. 5,000,185, which is a continuation-in-part of Ser. No. 834,893, Feb. 28, 1986, Pat. No. 4,794,931.

[51] Int. Cl.⁵ .............................................. A61B 8/12
[52] U.S. Cl. ............................................. 128/662.06
[58] Field of Search .................... 128/660.03, 660.09, 128/662.03, 662.06, 4, 6; 604/99-103

[56] References Cited

U.S. PATENT DOCUMENTS

| | | | |
|---|---|---|---|
| 3,817,089 | 6/1974 | Eggleton et al. | 128/662.06 |
| 3,938,502 | 2/1976 | Bom | 128/662.06 |
| 3,942,530 | 3/1976 | Northeved | 128/4 |
| 4,020,847 | 3/1977 | Clark, III | |
| 4,259,970 | 4/1981 | McLeod et al. | 128/662.06 |
| 4,275,597 | 6/1981 | Quedens et al. | 128/660.09 |
| 4,319,580 | 3/1982 | Colley et al. | 128/696 |
| 4,354,501 | 10/1982 | Colley et al. | 128/662.06 |
| 4,374,525 | 2/1983 | Baba | 128/4 |
| 4,391,282 | 7/1983 | Ando et al. | 128/4 |
| 4,408,612 | 10/1983 | Utsugi | 128/4 |
| 4,442,842 | 4/1984 | Baba | 128/6 |
| 4,466,443 | 8/1984 | Utsugi | 128/662.06 |
| 4,466,444 | 8/1984 | Baba | 128/21 |
| 4,475,553 | 10/1984 | Yamaguchi et al. | 128/4 |
| 4,489,727 | 12/1984 | Matsuo et al. | 128/6 |
| 4,489,728 | 12/1984 | Matsuo et al. | 128/4 |
| 4,494,549 | 1/1985 | Namba et al. | 128/4 |
| 4,546,771 | 10/1985 | Eggleton et al. | 128/662.05 |
| 4,572,201 | 2/1986 | Kondo et al. | 128/662.06 |
| 4,572,203 | 2/1986 | Feinstein | 128/662.06 |
| 4,576,177 | 3/1986 | Webster, Jr. | 128/660.03 |
| 4,582,067 | 4/1986 | Silverstein et al. | 128/662.06 |
| 4,587,972 | 5/1986 | Morantte, Jr. | 128/660.03 |
| 4,633,882 | 1/1987 | Matsuo et al. | 128/4 |
| 4,641,657 | 2/1987 | Ellis | 128/630 |
| 4,669,469 | 6/1987 | Gifford, III et al. | 128/662.06 |
| 4,732,156 | 3/1988 | Nakamura | 128/4 |
| 4,794,931 | 1/1989 | Yock | 128/662.06 |
| 4,841,977 | 6/1989 | Griffith et al. | 128/660.03 |
| 4,887,605 | 12/1989 | Angelsen et al. | 128/660.03 |
| 4,899,757 | 2/1990 | Pope, Jr. et al. | 128/662.06 |
| 4,917,097 | 4/1990 | Proudian et al. | 128/661.01 |
| 4,917,104 | 4/1990 | Rebell | 128/772 |
| 4,920,967 | 5/1990 | Cottonaro et al. | 128/772 |
| 4,928,699 | 5/1990 | Sasai | 128/6 |
| 4,951,677 | 8/1990 | Crowley et al. | 128/662.06 |
| 4,991,588 | 2/1991 | Pfleuger et al. | 128/772 |
| 4,998,916 | 3/1991 | Hammerslag et al. | 604/95 |
| 5,000,185 | 3/1991 | Yock | 128/662.06 |
| 5,002,059 | 3/1991 | Crowley et al. | 128/662.06 |
| 5,007,434 | 4/1991 | Doyle et al. | 128/772 |
| 5,049,130 | 9/1991 | Powell | 604/96 |
| 5,115,814 | 5/1992 | Griffith | 128/662.06 |

FOREIGN PATENT DOCUMENTS

| | | |
|---|---|---|
| 0088620 | 9/1983 | European Pat. Off. |
| 0163502 | 12/1985 | European Pat. Off. |
| 0234951 | 9/1987 | European Pat. Off. |
| 2305501 | 8/1974 | Fed. Rep. of Germany |
| 2424733 | 11/1979 | France |
| 8301893 | 6/1983 | PCT Int'l Appl. |

OTHER PUBLICATIONS

Slager et al. (1985), JACC, vol. 5, No. 6, pp. 1382-1386.
(List continued on next page.)

*Primary Examiner*—Francis Jaworski
*Attorney, Agent, or Firm*—Lyon & Lyon

[57] ABSTRACT

A catheter is provided for insertion into the blood vessel of a patient for ultrasonically imaging the vessel wall. The catheter includes a tubular element and an internally housed drive cable for effecting a circumferential scan about the catheter of an ultrasonic generating means. Both the tubular element and the drive cable are of a size and flexibility sufficient to permit their introduction into the vessel and subsequent advancement through the vessel to the location of the vessel wall where imaging is desired.

18 Claims, 4 Drawing Sheets

OTHER PUBLICATIONS

Wells (1966) World Medical Electronics, pp. 272-276.

Olson et al. (1974), IEEE Transactions on Biomed. Engin., pp. 168-171.

Omoto (1967), Jap. Heart J. 8:569-581.

Serruys et al. (1988) Am. J. Cardiol. 61:253-259.

Hisanaga et al. (1977) Proc. Jap. Soc. Ultrasonics Med. 32:43-44.

Wild et al. (1955) Am. Inst. Ultrasonics Med. (Aug.) pp. 47-72.

Garret, L. "A Catheter Assembly," PCT Application No. PCT/US82/01669 Published as WO83/01893 on Jun. 9, 1983.

Simpson, J. B. "Atherectomy Device & Method," European Patent Application No. 0 163 502, Published Apr. 12, 1985.

Wild et al., "Ultrasonic Ranging" Electronics 174-180 (Mar. 1955).

Ebina et al., "The Diagnostic Application of Ultrasound to the Disease in Mediastinal Organs," Sci. Rep. Res. Inst. Tohoku U. 12:199-212.

Wells, P. N. T., "Developments in Medical Ultrasonics," European Symposium on Medical Electronics, pp. 272-276 (Oct. 1975).

Kossoff, G., "Diagnostic Applications of Ultrasound in Cardiology," Aust. Radiol., X:101-6 (1966).

Omoto, R., "Ultrasonic Tomography of the Heart: An Intracardiac Scan Method" Ultrasonics, pp. 80-83 (Apr. 1967).

Omoto, R., "Intracardiac Scanning of the Heart with the Aid of Ultrasonic Intravenous Probe," Jap. Heart J. 8:569-581 (1967).

Eggleton et al., "Computerized Ultrasonic Visualization of Dynamic Ventricular Configurations," 8th ICMBE, Chicago, Ill. (Jul. 1969).

Hartley et al., "A Single-Crystal Ultrasonic Catheter-Tip Velocity Probe," Medical Instrumentation 8:241-243.

Hisanaga et al., "A New Real-Time Sector Scanning System of Ultra-Wide Angle . . . ," Proc. of the 22nd Annual Mtg. of the AIUM (1978).

Gichard et al., "Development of a Mechanically Scanned Doppler Blood Flow Catheter," Ultrasonics Symposium Proc. 75, CHO-994-4SU, pp. 18-21 (1975).

Wells et al., "Ultrasonic Transesophageal Measurement of Cardiac Output" Conference: Advances in Bioengineering, San Francisco, California (Dec. 1978).

Bertini et al., "Rotating Probe for Trans-Esophageal Cross-Sectional Echocardiography," J. Nucl. Med. Allied Sci. 28(2):115-121.

Fukuda, M., "Endoscopic Ultrasonography," In: Gill, R. W., Dadd, M. J., eds., WFUMB '85, 13-16 (1985).

Bom et al., "Ein Weg sur Intraluminaren Echoarteriographie" Untraschall 8 pp. 233-236 (Oct. 1987) (translation attached).

Isner, et al., "Percutaneous Intravascular US as Adjunct to Catheter-Based Interventions: . . . Radiology," 1990; 175(1):61-70.

Crowley, et al., "Optimized Ultrasound Imaging Catheters for use in the Vascular System," Int. J. Card. Imag. 1989; 4:145-151.

Bom et al., "Early and Recent Intraluminal Ultrasound Devices," International Journal of Cardiac Imaging, 4:79-88 (1989).

Hisanaga et al., Transesophageal Cross-sectional Echocardiography, American Heart Journal, Nov. 1980, pp. 607-609.

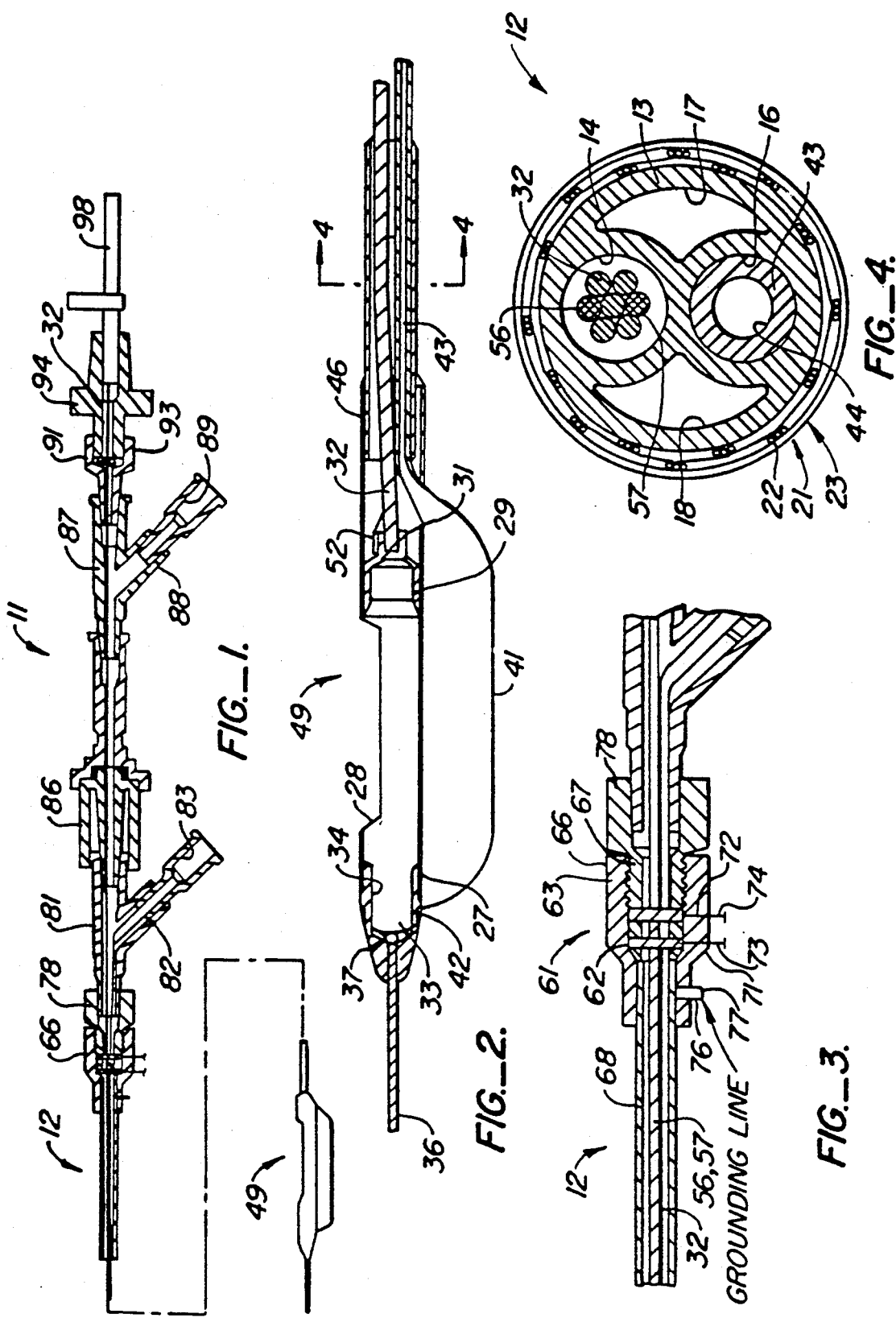

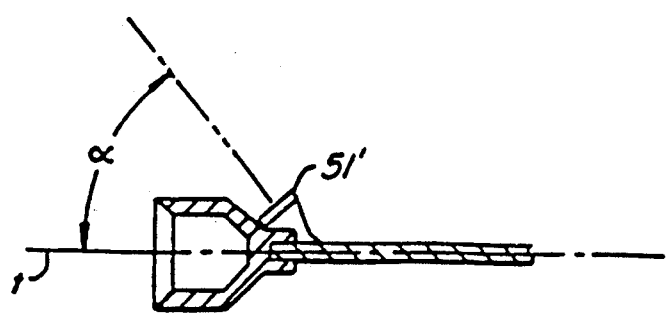
FIG._2A.
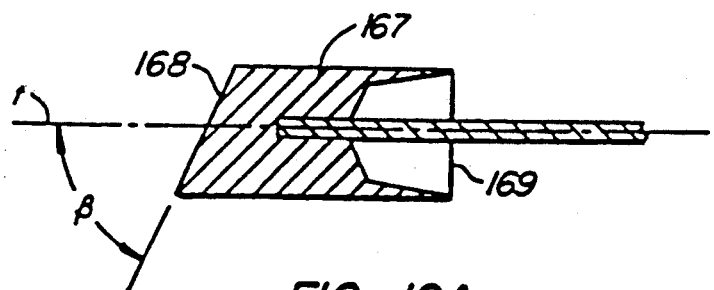
FIG._10A.
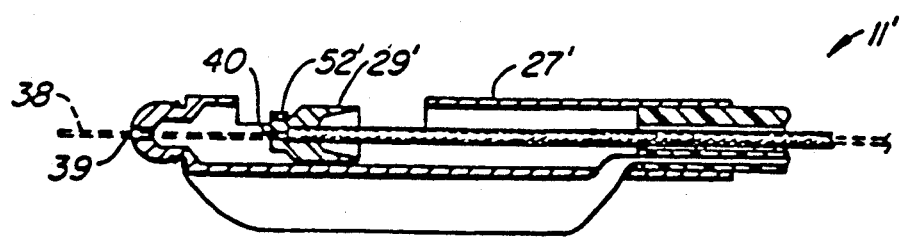
FIG._2B.
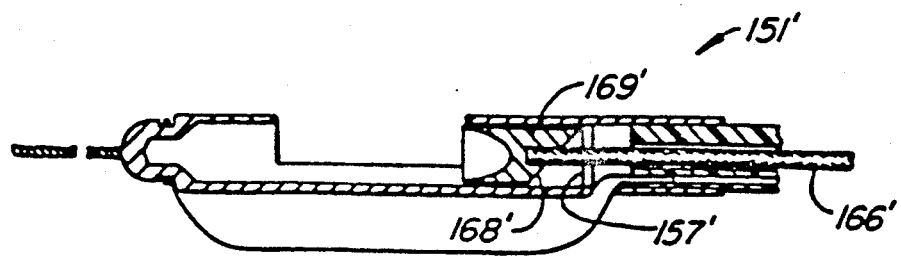
FIG._10B.

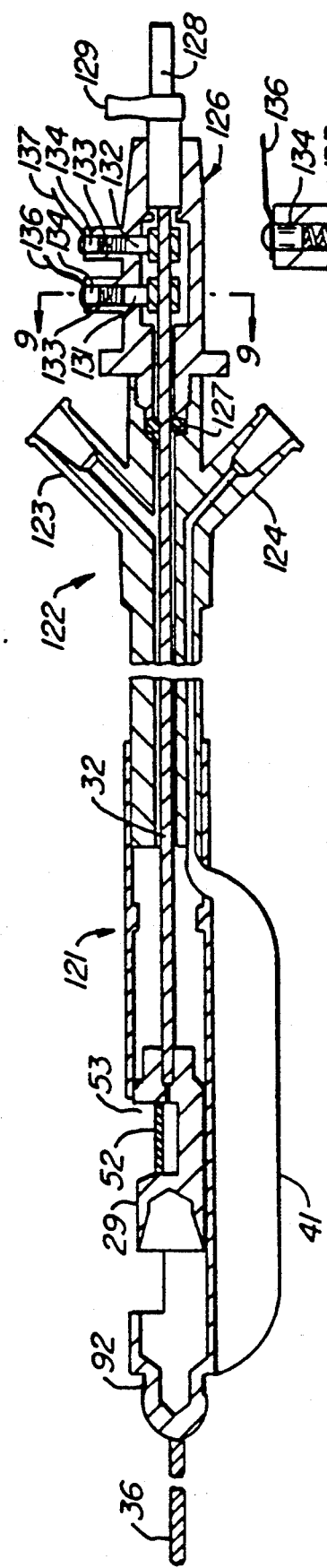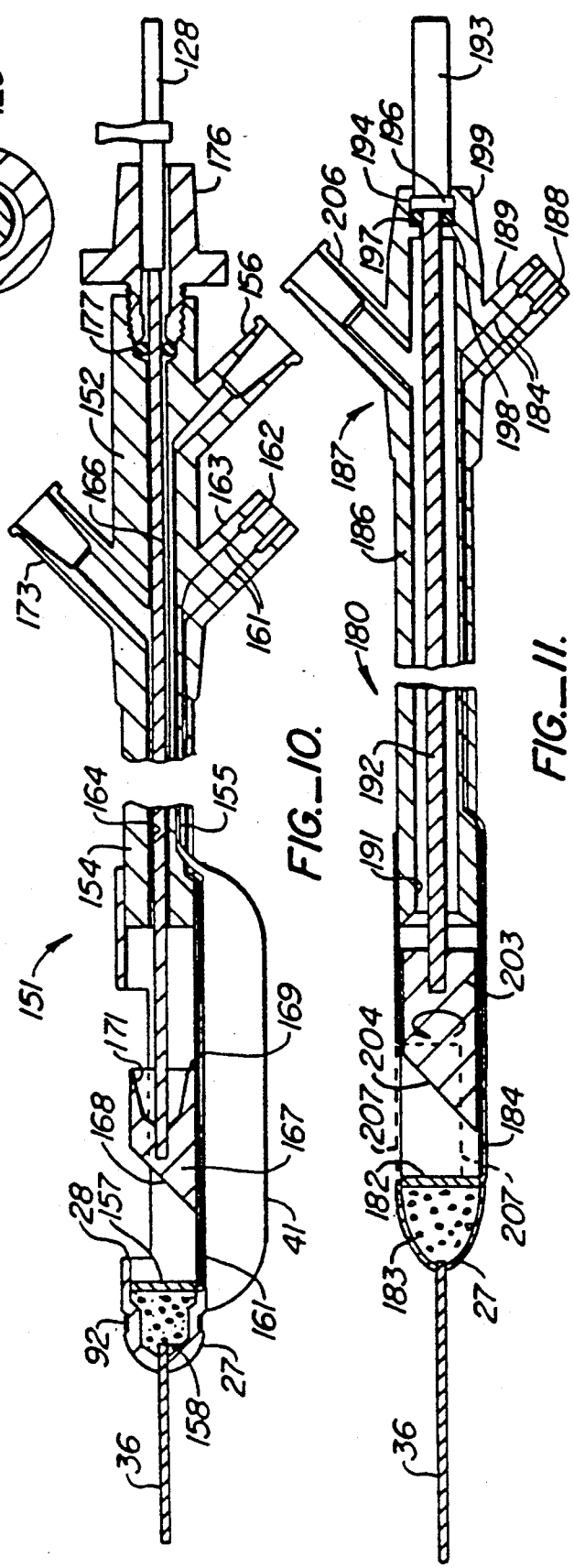

1

METHOD AND APPARATUS FOR INTRAVASCULAR TWO-DIMENSIONAL ULTRASONOGRAPHY

This application is a continuation of co-pending U.S. application Ser. No. 826,260, filed Jan. 24, 1992, which is a continuation of co-pending U.S. application Ser. No. 649,048, filed Feb. 1, 1991, abandoned, which is a continuation of application Ser. No. 07/290,533 filed on Dec. 23, 1988, now U.S. Pat. No. 5,000,185, which is in turn a continuation-in-part of U.S. application Ser. No. 06/834,893 filed on Feb. 28, 1986, now U.S. Pat. No. 4,794,931. The entire disclosures of the aforementioned patents and applications are incorporated herein by reference. The present application is related to U.S. application Ser. No. 07/290,217 filed on Dec. 23, 1988, commonly assigned herewith, the disclosure of which is incorporated herein by reference.

BACKGROUND OF THE INVENTION

This invention relates to a catheter apparatus, system and method for intravascular two-dimensional ultrasonographic imaging and more particularly to such an apparatus, system and method for guiding and monitoring interventional therapy to reduce vascular stenosis.

Ultrasonic two-dimensional imaging apparatus and systems have heretofore been provided for use in endoscopy for examining the gastrointestinal tract. Such a device is disclosed in U.S. Pat. No. 4,494,549. Such devices, however, have been relatively large and inflexible and are completely unsuitable for use within the vascular system of the human body. In addition, there is no provision for guiding such devices into specific branches of blood vessels.

There is therefore a need for a new and improved catheter apparatus, systems and methods which can be utilized for performing intravascular two-dimensional ultrasonographic imaging. It would be particularly desirable if such imaging apparatus and methods could be combined with a variety of intravascular therapeutic modalities, such as angioplasty, atherectomy, laser ablation, and the like, in order to provide simultaneous imaging and recanalization procedures.

SUMMARY OF THE INVENTION

According to the present invention, a method for imaging the interior of a blood vessel comprises scanning an ultrasonic signal in a preselected pattern about said interior. By receiving ultrasonic energy reflected from the interior surface of the vessel, including any stenosis or occlusion present, an image or profile of the blood vessel may be produced. Conveniently, the ultrasonic signal is generated by a transducer located at the distal end of a vascular catheter comprising a flexible tubular member. The transducer may be manipulated directly to sweep the ultrasonic signal in a desired pattern, including radial, planar and conical. Alternatively, the transducer may be fixed within the catheter and a reflective surface manipulated to sweep the ultrasonic signal in a desired pattern. The imaging method of the present invention is advantageously combined with interventional therapeutic techniques to reduce vascular stenosis, where the stenosis may be imaged prior to, during, and after intervention to help direct the interventional activity to where it will be most effective.

In general, it is an object of the present invention to provide a catheter apparatus, system and method for intravascular two-dimensional ultrasonography.

Another object of the invention is to provide an apparatus, system and method of the above character which has a high resolution capability.

Another object of the invention is to provide an apparatus, system and method of the above character which can be utilized for assessing endovascular lesions.

Another object of the invention is to provide an apparatus, system and method of the above character which can be utilized for monitoring the results of interventional therapy.

Another object of the invention is to provide an apparatus, system and method of the above character which can be used with angioplasty, atherectomy, laser ablation, drug delivery and similar vascular interventional methods and devices.

Another object is to provide an apparatus, system and method capable of selective cannulation of branch vessels.

Additional objects and features of the invention will appear from the following description in which the preferred embodiments are set forth in detail in conjunction with the accompanying drawings.

BRIEF ON OF THE DRAWINGS

FIG. 1 is a side elevational view partially in cross-section of a catheter apparatus incorporating the present invention.

FIG. 2 is an enlarged cross-sectional view of the distal extremity of the apparatus shown in FIG. 1.

FIG. 2A is a detail view illustrating an alternate mounting of a crystal transducer to provide a conical sweep pattern.

FIG. 2B is an alternate embodiment of the distal extremity of the apparatus shown in FIG. 1, modified to be inserted over a movable guidewire and with the cutting direction reversed.

FIG. 3 is an enlarged cross-sectional view of an intermediate portion of the apparatus shown in FIG. 1.

FIG. 4 is an enlarged cross-sectional view taken along the line 4—4 of FIG. 1.

FIG. 8 is an enlarged cross-sectional view of another embodiment of a catheter apparatus incorporating the present invention.

FIG. 9 is a cross-sectional view taken along the lines 9—9 of FIG. 8.

FIG. 10 is an enlarged cross-sectional view of still another embodiment of a catheter apparatus incorporating the present invention.

FIG. 10A is a detail view illustrating an alternate configuration of a reflective surface to provide a conical sweep pattern.

FIG. 10B is an alternate embodiment of the distal extremity of the catheter apparatus of FIG. 10, modified to provide a fixed ultrasonic transducer located proximally of a reflective surface on a cutter.

FIG. 11 is an enlarged cross-sectional view of another embodiment of the catheter apparatus incorporating the present invention.

DESCRIPTION OF THE SPECIFIC EMBODIMENTS

Figure 5:
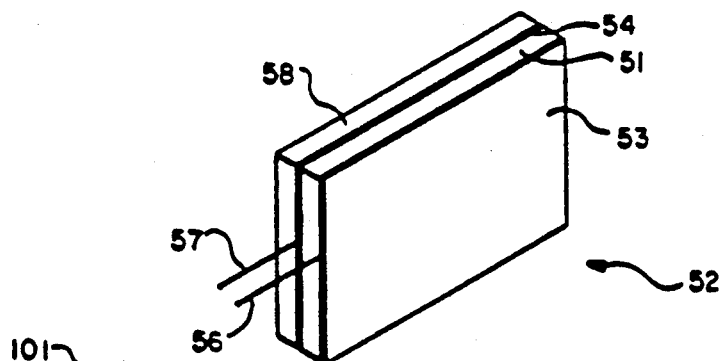
FIG. 5 is an isometric view of the crystal assembly which forms a part of the apparatus shown in FIG. 1.

In general, the catheter apparatus of the present invention includes a flexible tubular element which is adapted to be inserted into a blood vessel in the vascular system and a flexible rotatable elongate element which is disposed in the tubular element. In a first embodiment, an ultrasonic transducer is carried at the distal end of the flexible rotatable elongate element, and electrical circuitry carried at the distal end of the flexible tubular element is connected to the ultrasonic transducer for supplying signals to and receiving signals from the transducer. In a second embodiment, a reflective surface is carried by the distal end of the flexible rotatable elongate element, and the ultrasonic transducer is mounted in the distal tip of the flexible tubular element so that signals generated by the transducer will be reflected by the reflective surface. In both embodiments, a transmitter is provided for supplying signals to the ultrasonic transducer and a receiver is provided for receiving signals from the ultrasonic transducer. A motor drive is usually provided for rotating the flexible elongate element, along manual rotation may also be employed. By rotating the flexible elongate element, the transducer signal can be swept in a desired pattern, either directly by the transducer in the first embodiment or indirectly by the reflective surface in the second embodiment. Timing and control circuitry is provided for controlling the operation of the transmitter and receiver and optionally the motor drive. A display is provided which is operated under the control of the timing and control circuitry for displaying the image information which is received by the receiver.

The catheters of the present invention may further include interventional capability for recanalization of occluded regions within the imaged blood vessel. Recanalization is intended to refer to both the opening of total occlusions as well as broadening of the vessel lumen in partial occlusions. Catheters combining ultrasonic imaging capability with atherectomy devices for severing of stenotic material are described in detail hereinafter. The methods of the present invention, however, are not limited to atherectomy and include a wide variety of other interventional techniques which may be performed with vascular catheters. Suitable interventional techniques include balloon angioplasty, laser ablation angioplasty, balloon embolectomy, aspiration embolectomy, heat probe ablation, abrasion, drilling, therapeutic ultrasound, and the like. Also, the catheters may be adapted for introducing clot-dissolving drugs, such as tissue plasminogen activator, streptokinase, urokinase, and the like, in order to reduce the stenosis, as well as platelet-receptor blockers and drugs which limit cell multiplication in order to inhibit restenosis. Conveniently, perfusion lumens and ports may be provided in the catheter to provide for the administration of such drugs.

A first exemplary construction of a catheter apparatus 11 constructed in accordance with the principles of the present invention comprises an elongate tubular assembly 12, as illustrated in FIGS. 1-4. The elongate tubular assembly 12 includes an elongate flexible tubular element 13 which is provided with four lumens 14, 16, 17 and 18, with the lumen 14 serving as a torque tube, lumen 16 serving as a balloon tube and lumens 17 and 18 serving as infusion tubes or lumens as hereinafter described. The tubular element 13 may conveniently be formed as a single extrusion which provides the four lumens, with the lumens 14 and 16 being substantially circular in cross-section and the lumens 17 and 18 being arcuate in shape with the configuration of each being determined by three arcs with one of the arcs being concentric with the outer diameter of the tubular element 13 and with the two smaller arcs being concentric with lumens 14 and 16 respectively.

A braided shield 21 is provided on the exterior of the tubular element 13 and takes the form of one or more layers of braided strands 22 formed of a suitable magnetic material such as an electrical shield. A cover tube 23 covers the braided shield 21 and extends the length of the tubular element 13. The cover tube 23 can be formed of a suitable material such as a heat shrinkable plastic which is shrunk tightly onto the braided shield 21 and provides a smooth outer surface so that the tubular assembly 12 can readily enter a vessel of the vascular system of a patient.

A work performing device such as an atherectomy or cutting device of the type described in European patent application 163 502 may be provided in the distal extremity of the tubular assembly 12. A suitable cutting device is described in said European application and consists of a housing 27 which is provided with a cutout 28. A rotary cutter 29 is rotatably disposed within the housing 27 and is provided with a hub 31 that is secured to a flexible rotatable torque cable 32. The cable 32 is disposed in and extends through the torque tube lumen 14. The torque cable 32 is formed of a suitable material such as stainless steel. The housing 27 is provided with a rounded tip 33 having a recess 34 which is adapted to receive material which is removed by the rotary cutter 29 as the cutter 29 is advanced as hereinafter described. A spring tip guide or guidewire 36 capable of being shaped is secured to the rounded tip 33 and extends forwardly therefrom and serves to guide or steer the housing 27 as the tubular assembly 12 with the cutting device 26 secured thereto is introduced into the vessel of the vascular system of the patient. As shown, the spring tip guide 36 can be secured to the rounded tip 33 by suitable means such as solder 37. It thus can be seen that the guidewire 36 is associated with the housing 27. Alternatively, a movable guidewire 38 (FIG. 2B) can be utilized to facilitate steering of the catheter 11 into the desired vessel of the patient.

A balloon 41 of an expandable type is optionally secured to the housing in a region opposite the cutout 28 and has its distal extremity bonded around the tip 33 by suitable means, such as an adhesive 42. As shown in FIG. 2, the balloon 41 underlies substantially the entire length of the housing 27. The balloon 41 is in communication with a balloon tube 43 which extends through the balloon tube lumen 16 in the tubular element 13. The balloon tube 43 is provided with a lumen 44 through which a medium can be introduced for inflating the balloon 41 and removed for deflating the balloon 41. The proximal extremity of the balloon 41 and the proximal extremity of the housing 27 is secured to the distal extremity of the tubular assembly 12 by suitable means, such as heat shrinkable tubing 46.

A system 49 is provided at the distal end 49 of catheter 11 for imaging the region in which the work performing device is located, said system usually being—a two-dimensional ultrasound image system. The system 49 includes an ultrasonic transducer, such as a single crystal 51 (see FIG. 5), which is mounted on the hub 31 and is secured thereto by suitable means such as an adhesive. The crystal 51 is part of an assembly 52. The crystal 51 should be capable of operating at a frequency range of 5 to 50 megahertz and typically can be formed of a suitable material such as barium titanate or cinnabar. As can be seen from FIG. 5, the crystal 51 has a rectangular block-like configuration and has two opposed surfaces covered by metallic conducting films 53 and 54 formed of a suitable material such as chrome or gold. The material of the films can be formed of a foil or can be in the form of films evaporated or sputtered onto the opposite surfaces of the crystal 51. The films 53 and 54 serve as electrodes and are connected to connecting wires 56 and 57 by suitable means such as solder. Means is provided for damping out the oscillations from the backside of the crystal 51 and takes the form of a rectangular block 58 formed of a suitable backing material. The backing material can be formed in a conventional manner so as to cancel out oscillations from the side of a crystal in which the backing material is disposed.

The present invention, however, is not limited to the use of piezoelectric crystal oscillators as the ultrasonic transducer, and organic electrets such as polyvinylidene difluoride (PVDF) and vinylidene fluoride—trifluoroethylene copolymers may also find use. PVDF is particularly suitable as a transducer at higher frequencies, typically at or above 40 MHz.

The wires 56 and 57 are braided onto the torque cable 32 and rotate with the torque cable. The wires 56 and 57 extend towards the proximal extremity of the tubular assembly 12 and extend into a fitting 61 (see FIG. 3) formed of a suitable material such as plastic. A pair of spaced-apart slip rings 62 and 63 formed of a conducting material such as copper are secured to the torque cable 32. The wire 56 is bonded to the slip ring 62 and the wire 57 is bonded to the slip ring 63. A fitting 66 is provided which has a threaded bore 67. The tubular assembly 12 extends through the fitting 66 and a reinforcing sleeve 68 extends over the portion of the tubular assembly 12 extending therethrough. A pair of spring urged contacts 71 and 72 are carried by the fitting 66 and are adapted to slidably engage the slip rings 62 and 63. The contacts 71 and 72 are connected to conductors 73 and 74. A grounding lug 76 is provided on the fitting 66 and makes electrical contact with the braided shield 21. A conductor 77 is connected to the grounding lug 76.

Figure 6:
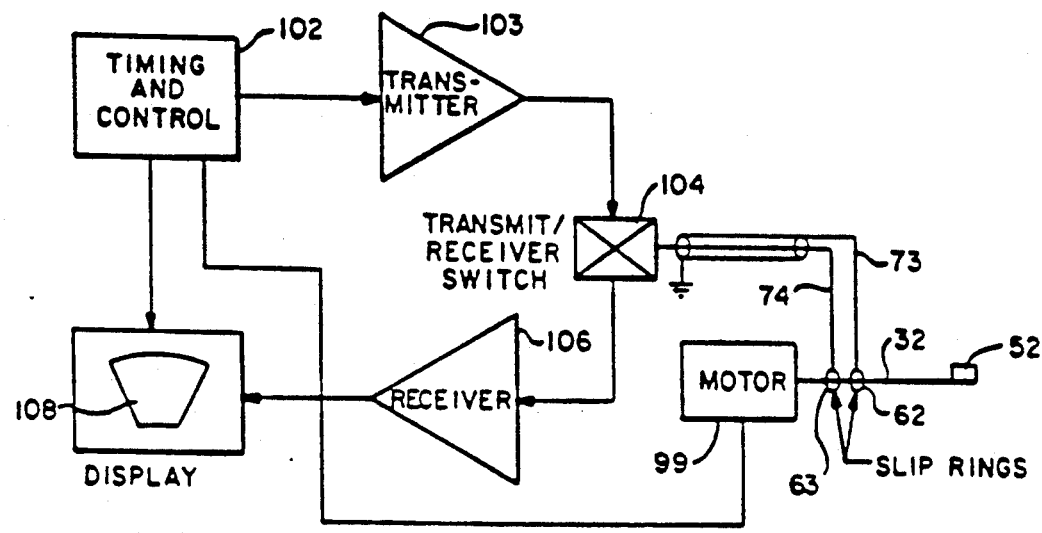
FIG. 6 is a schematic block diagram of the electrical and electronic apparatus utilized in the system.

A male fitting 78 (see FIG. 1) is threaded into the threaded bore 67. A single arm adapter 81 is mounted in the male fitting 78 and carries an arm 82 having thereon a balloon inflation port 83 that is in communication with the lumen 44 in the balloon tube 43 disposed in the tubular assembly 12. The single arm adapter 81 is secured to a rotating adapter 86 of a conventional type and through which the tubular assembly 12 extends. Another single arm adapter 87 is mounted in the rotating adapter and is provided with a side arm 88 having an infusion port 89 disposed therein which is in communication with the infusion lumens 17 and 18 provided in the tubular assembly 12. A tapered fitting 91 is mounted in the single arm adapter 87 and is provided with a threaded bore 92 which carries an O-ring 93 that is adapted to be engaged by a male type fitting 94 to form a liquid-tight seal between the tubular assembly 12 and the torque cable 32 which extends therethrough. The torque cable 32 is secured to a suitable drive member such as a clutch member 98 of the type described in European application 163 502 and U.S. Pat. No. 4,771,774, the disclosures of which re incorporated herein by reference. The clutch member 98 is adapted to be secured to a motor drive means of the type described in U.S. Pat. No. 4,771,774 consisting of a motor drive unit which in the present application is identified as a motor 99 (see FIG. 6). The motor 99 is driven by and is under the control of electronic circuitry forming a part of system 49. The part of the system 49 shown in block diagram form is substantially conventional and can be of a suitable type such as certain equipment identified as Model 851B manufactured by Advanced Technology Laboratories, Inc. of Bothel, Washington. As shown in FIG. 6, such apparatus includes a timing and control block 102 which supplies pulses to a transmitter 103. The output of the transmitter 103 is supplied through a transmit receive switch 104 which supplies the signals on the conductors 73 and 74 through the slip rings 62 and 63 onto the conductors 56 and 57 connected to the crystal 51. During the time that the transmitter 103 is supplying high frequency energy to the crystal, the crystal 52 is being rotated by the motor driving the torque cable 32 with the motor 99 being under the control of the timing and control block 102. The motor 99 is of a type such as an open loop stepping motor or a closed loop servo controlled motor which can be driven by the timing and control block 102.

As an alternative to the use of an external motor 99 connected to the cutter 29 by torque cable 32, it would be possible to construct catheters according to the present invention utilizing micromotors within the distal extremity of the catheter. The micromotors could be attached to directly rotate the cutter and transducer (or reflective surface as described hereinafter), typically by mounting at the end of a non-rotating cable analogous to torque cable 32.

Figure 7:
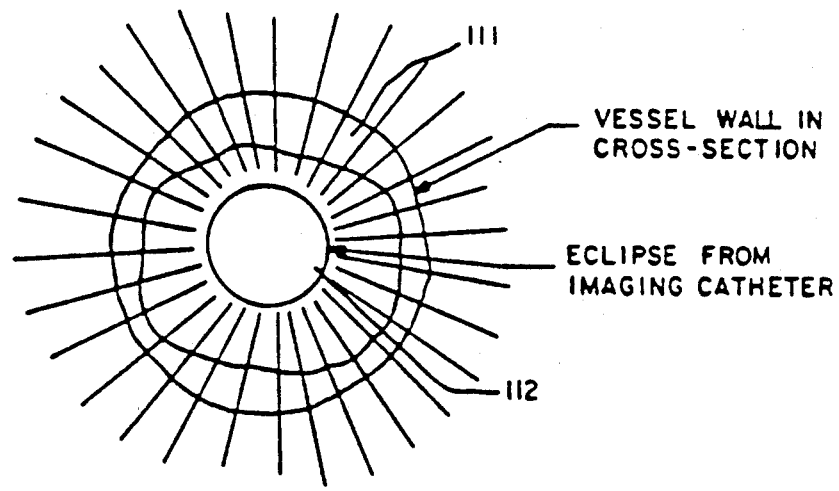
FIG. 7 is a two-dimensional display of an ultrasonogram which can be obtained with the apparatus and system shown in FIGS. 1–6.

The transmitter generates a voltage pulse, typically in the 10 to 50 volt range, for excitation of the transducer crystal 51. Supplying such voltage pulses to the crystal causes the transducer to produce sonic waves which emanate therefrom into the surrounding tissue structure. Portions of the sonic energy wave are reflected by the tissue structure back to the transducer and the transducer 51 acts as a receiver and picks up the sonic vibrations and converts them into electrical signals which are supplied by the conducting wires 56 and 57 back to the slip rings 62 and 63 through the conductors 73 and 74 and through the transmit receive switch 104 to a receiver 106. These signals are amplified and supplied to a display unit 107 which includes a CRT screen 108 under the control of the timing and control block 102 to supply an image 109 on the display 108 which can be of the type shown in FIG. 7. As can be seen from FIG. 7, as viewed through 360°, the vessel wall 111 of the image 109 is shown as indicated, having different cross sections depending upon the build-up of plaque therein. A central region 112 of the image is eclipsed because of the imaging catheter. Alternatively, if desired, only a sector of a lesser angle than 360° can be viewed.

The catheter apparatus of the present invention can be constructed in various sizes. For example, in a 9 French size, the balloon can have a length of approximately 3 centimeters. Sizes down to 3 French and below can be accomplished with the construction of the present invention. These particular dimensions are exemplary only and not intended to limit the scope of the present invention in any way.

Operation and use of the catheter apparatus, system and method during intravascular ultrasonography can now be briefly described as follows. Let it be assumed that it is desired to utilize the apparatus, system and method of the present invention to remove the atheroma in a blood vessel of a patient. The catheter of the catheter apparatus of the present invention is introduced into a vessel of the patient as, for example, into the femoral artery and introducing the catheter into the artery by the use of the guidewire 36. The progress of the catheter into the vessel of the patient can be observed under x-ray fluoroscopy. As soon as the cutting device has entered into a region which is desired to remove certain material from the vessel and before a cutting operation is commenced, the atheroma itself can be viewed by operation of the ultrasonic imaging system 49. This can be accomplished by operating the timing control block 102 to cause operation of the motor 99 which in turn causes rotation of the torque cable 32 and the crystal assembly 52 to scan the interior of the vessel in which the crystal 51 is disposed, usually at a rotation rate in the range from about 100 to 20,000 rpm, more usually from about 500 to 2,000 rpm. An image of what is being scanned will appear on the screen 108 of the display device 107. Alternatively, the torque cable 32 may be manually rotated (or aimed without rotation) to provide a desired image. Generally, however, motorized rotation will provide a higher definition image. During the time this rotary scanning is taking place, the cable 32 can be advanced to advance the cutter so that the entire region in which the material is to be removed can be scanned. Usually, the cable 32 is advanced incrementally so that distinct cross-sectional images will be successively produced, allowing the operator to determine the length and topography of the region. Alternatively, the entire catheter apparatus 11 may be axially advanced or retracted within the blood vessel lumen to provide a plurality of cross-sectional images to allow assessment of the entire length of the atheroma.

After the scan, the cable 32 can be retracted slightly (or the catheter 11 repositioned) so that the proximal extremity of the cutout 28 lies at the proximal extremity of the atheroma. In order to stabilize the cutting device, the balloon 41 can be inflated so as to urge the cutout 28 of the housing 27 towards the portion of the atheroma it is desired to remove. The motor 99 can then be energized to rotate the cutter 29. As the cutter 29 is rotated, it can be advanced to progressively remove the material which is disposed within the cutout 28 of the housing 27. As this material is removed it is pushed forwardly and eventually moves into the recess 34. The balloon 41 can then be deflated and the catheter apparatus removed from the vessel after which the material which has been deposited in the recess 34 can be removed and the cutting device cleaned for reinsertion into the vessel of the patient for removal of additional material from the vessel if required.

During the time that the cutting operation is taking place, the cutting operation can be viewed ultrasonically by the rotating crystal 51 which places an image on the screen 108. From this image it can be ascertained how well the cutter is performing in removing the material and whether or not an additional pass of the cutter is required. It should be appreciated that if necessary, several passes of the cutter can be made and, if necessary, the catheter assembly can be removed from the vessel of the patient to clean out material which has been removed and deposited in a recess 34.

As illustrated in FIG. 2, the ultrasonic transducer 51 is oriented to direct the ultrasonic signal in a direction substantially radially outward relative to the axis of the flexible tubular element 13. It will sometimes be desirable, however, to incline the ultrasonic transducer relative to the tubular axis, as illustrated at 51' in FIG. 2A. By inclining the transducer 51', the ultrasonic signal is directed at a forward angle α relative to the tubular axis. By rotating the inclined transducer 51', the ultrasonic signal will sweep a conical pattern directed forward of said transducer. The angle α may be in the range from about 10° to 85°, usually being in the range from 20° to 60°. Scanning with a conical sweep is desirable because it can provide forward viewing at or in front of the location where the cut is being made.

An alternate embodiment 11' of catheter 11 is illustrated in FIG. 2B. The catheter 11' is similar to that of catheter 11, except that it is modified to permit insertion of the catheter 11' over a movable guidewire 38 and the cutter 29' is reversed to provide cutting when the cutter is translated in the proximal (rearward) direction. The modifications include providing a penetration 39 in the distal tip of housing 27 and an axially-aligned penetration 40 in the cutter 29'. The ultrasonic transducer 52' is mounted on the distal end of cutter 29', and torque cable 32' includes an axial lumen. In this way, the catheter 11' is inserted by conventional techniques over guidewire 38, with the guidewire passing through penetrations 39 and 40 and the lumen of torque cable 32°.

Another embodiment of the catheter apparatus of the present invention is shown in FIGS. 8 and 9. Many of the parts are very similar to the parts utilized in the embodiment of the invention shown in FIG. 1 and have been given the corresponding numerals. The ultrasonic transducer 52 is mounted in a cavity 53 formed to the rear of the rotary cutter 29. The distal extremity of the catheter apparatus shown in FIG. 8 (i.e., to the left) differs from the apparatus shown in FIG. 1 in that the conducting wires or leads connected to the ultrasonic crystal 52 are connected to the outside world at a point which is proximal of an adapter 122 whereas in the embodiment shown in FIG. 1, the connectors are connected at a point which is distal of the adapters 82 and 88. Thus there is shown an adapter 122 which is provided with an arm 123 through which dye injection and pressure measurements can be made and another fitting 124 which can be utilized in inflating and deflating the balloon 41. Another adapter 126 is provided which is threaded into the proximal end of the adapter 122 and forms a sealing engagement with an O-ring 127 carried by the adapter 122. The torque cable 32 extends through the adapter 126 and is connected to a clutch member 128. The clutch member 128 which carries a finger operated member 129 is adapted to be secured to motorized drive means of the type hereinbefore described for causing rotation of the torque cable 32.

As hereinbefore explained, the conducting wires connected to the ultrasonic transducer 52 are braided into the guidewire 32. Means is carried by the adapter 126 which is adapted to make contact with the conducting wires connected to the crystal 52 and consists of brushes 131 and 132 which are yieldably urged by springs 133 towards the torque cable 32 so as to make contact with the conducting wires or leads carried by guidewire 32. The springs 133 are held in place by pins 134 which are frictionally seated within the adapter 126. Conducting wires 136 and 137 are connected to the pins 134. These wires 136 and 137 are connected into the system in a manner hereinbefore described with the previous embodiments. The operation of this embodiment is very similar to that described in conjunction with the operation of the embodiment shown in FIG. 1.

Operation of this embodiment of the invention is very similar to that hereinbefore described with the principal advantage being that leads which are connected to the crystal and for receiving signals from the crystal are disposed proximally of the two arm adapter 122.

As a modification of catheter 121, cutter 29 could be provided with an abrasive external surface, either in place of or in addition to the forward cutting edge. Such an abrasive surface would be useful to remove atheroma and plaque by contact abrasion.

Still another embodiment 151 of the catheter apparatus of the present invention is shown in FIG. 10. Certain parts of this catheter apparatus 151 are very similar to those hereinbefore described and are identified by the same numbers. Thus there has been provided a housing 27 which has an outwardly facing cutout 28. A coil spring guide wire 36 is secured to the distal extremity of the housing 27 as shown (although the catheter 151 could easily be adapted to receive a movable guidewire as described above in connection with the embodiment of FIGS. 1-4). The balloon 41 is carried by the housing and has its distal extremity secured to the housing by a band 92. The balloon 41 is disposed outside of the housing 27 on the side opposite the cutout 28. A flexible tubular assembly 154 is secured to the proximal end of the housing 27. A three-arm adapter 152 is mounted on the proximal extremity of the tubular assembly 154. The tubular assembly 154 comprises a flexible tubular element formed of a suitable material such as plastic which is provided with a balloon inflation lumen 155 that is in communication with the interior of the balloon 41 and extends into a balloon inflation port 156 provided as a part of the three-arm adapter 152.

A crystal 157 is carried by the housing 27 in a stationary position. As shown, the crystal 157 is mounted vertically or in a direction which is at right angles to the longitudinal axis of the housing 27. It can be mounted in the distal extremity of the housing 27 in a suitable manner such as by an adhesive. A suitable sound absorbing material 158 is provided behind the ultrasonic crystal 157 and fills the space between the crystal 157 and the distal extremity of the housing 27. A pair of conducting wires 161 are connected to the ultrasonic crystal 157 and extend rearwardly through the housing 27 and are connected into sockets 162 provided in a side arm 163 forming a part of the adapter 152.

The flexible tubular element 154 is provided with a large lumen 164 extending the length thereof and which has a rotatable flexible drive cable 166 disposed therein. The flexible torque cable 166 is formed in the manner hereinbefore described and is secured to a generally cylindrical member 167 which as hereinafter described, serves as a reflector mount and also serves to carry a rear-facing rotary cutter 169. Thus as shown, the member 167 is provided with a reflective surface 168 which is inclined at an angle of approximately 45° and faces the transducer 157 in such a manner so that sound waves propagated by the transducer impinge upon the surface 168 and are propagated outwardly in a direction substantially transverse, i.e., at right angles, to the longitudinal axis of the housing 27. A circular cutting edge 169 is provided on the member 167 at the proximal extremity thereof. A truncated conical recess 171 is provided in the proximal extremity of the member 167. The conical recess 171 can be used as a reservoir for collecting material as it is severed by the circular cutting edge 169.

The angle of inclination of the reflective surface 168 relative to the axis of housing 27 may be varied, particularly being increased, as illustrated in FIG. 10A, where angle $\beta$ may be in the range from 10° to 85°, usually being in the range from 10° to 40°. By inclining the reflective surface by an angle $\beta$ less than 45°, the reflected ultrasonic signal will sweep in a rearward conical pattern which allows viewing at or in front of (i.e., to the right in FIG. 10) the cutting edge 169 of member 167.

The three-arm adapter 152 is provided with another arm 173 which serves as an infusion port and which is in communication with the lumen 164 through which the drive cable 166 extends. This lumen 164 opens into the interior of the housing 27 and is in communication with the cutout 28. Another adapter 176 is threaded into the proximal extremity of the adapter 162 and engages an O-ring 177. The drive cable 166 extends through the adapter 176 and has its distal extremity secured to the clutch member 128. As hereinbefore explained, the clutch member 128 can be secured to a motorized drive means (or may be manually rotated) for causing rotational movement of the cutter and mirror member 167.

An alternate embodiment 151' of catheter 151 is illustrated in FIG. 10B. The catheter employs a fixed ultrasonic transducer 157', but cutter 169' is reversed to provide for forward cutting. Forward cutting is often advantageous in that severed stenotic material is less likely to become entangled with the torque cable 166'. Ultrasonic transducer 157' will be provided with a central penetration to allow passage of the torque cable 166', and said transducer will be located at the proximal end of housing 27', but otherwise the construction of catheter 151' will be the same as catheter 151.

In a further modification, it is possible to secure the ultrasonic transducer 157' onto the torque cable 166'. Wires connecting the transducer 157' to the external receiver and transmitter would then be attached to the torque cable 166' and coupled to the outside in a manner similar to that illustrated in FIGS. 1-4. The transducer 157' would then translate axially in tandem with the cutter 169' and the mirror 168'. By maintaining a fixed distance between the cutter 169' and transducer 157', signal processing to produce an image is simplified.

Operation of the catheter apparatus 151 shown in FIG. 10 may now be described as follows. The operation of this device in many respects is very similar to that hereinbefore described with respect to the placement of the catheter in the vessel. The housing 27 can be positioned in the stenosis hereinbefore described and ultrasonic imaging can be carried out by supplying pulses of electrical energy to the ultrasonic transducer 157 which emanates ultrasonic energy and directs the same onto the reflector 168 which reflects the ultrasonic energy up into the tissue surrounding the housing. Rotation of the mirror 168 causes an image to be formed which can be viewed in the manner hereinbefore described. This imaging can be carried out by rotating the cable 166 and at the same time advancing the drive cable 166 throughout the length of the cutout 28 to view the stenosis. After the viewing operation has been accomplished and it is ascertained that it is desirable to remove the material creating the stenosis by use of the work performing device in the form of the cutter member 167, the cutter member 167 can be advanced to the distal extremity of the cutout 28. With the cutout 28 in the proper location, the balloon 41 can then be inflated through the balloon inflation port 156 to urge the housing 27 in a direction so that the stenosis enters the cutout. As soon as this has been accomplished, the cutter member 157 can be rotated at a high rate of speed and gradually retracted (i.e., translated to the right in FIG. 10) to cause the material forming the stenosis to be severed by the blade 169 on cutter member 167 and collected within the recess 171. This cutting and collecting operation can be continued until the cutter member 167 has been advanced to the extreme proximal position. At this time, the catheter apparatus 151 can be removed and the tissue collected within the recess 171 can be removed. Thereafter, additional insertions of the catheter apparatus can be made and the same cutting operations performed until desired amount of material has been removed from the area of the stenosis to provide for increased blood flow through the vessel.

Another embodiment of a catheter apparatus 180 incorporating the present invention is shown in FIG. 11. The catheter apparatus 180 is utilized solely for imaging purposes and employs a fixed ultrasonic transducer 182 which transmits its signal against a rotating reflective surface 204. The catheter apparatus 180 is constructed very similar to the catheter apparatus 151 shown in FIG. 10 with the exception that the cutting mechanism has been eliminated. The use of such a catheter apparatus 180 is desirable where it is unnecessary to provide a cutting function (or other interventional treatment modality). The catheter apparatus 180 also has many parts which are similar to the catheter apparatuses heretofore described. Thus there is provided a housing 27 which carries on its distal extremity a coil spring guide 36. As before, however, the catheter 180 can also be adapted to be inserted over a movable guidewire within the scope of the present invention. The ultrasonic transducer 182 is provided in the distal extremity of the housing 27 and is disposed vertically or in a direction which is perpendicular to the longitudinal axis of the housing. A sound absorbing backing material 183 is provided in the distal extremity of the housing behind the transducer 182. Conducting wires or leads 184 are connected to the transducer 182. The proximal extremity of the housing 27 is connected to the distal extremity of flexible elongate tubular element 186 which is connected to a two-arm adapter 187. The leads 184 extend through the tubular element 186 and are connected to sockets 188 provided in the arm 189 of the two-arm adapter 187. The tubular element 186 is provided with a large lumen 191 which carries the drive cable 192. The drive cable 192 is connected to a clutch member 193 of the type hereinbefore described which is adapted to be driven by motive means in the manner hereinbefore described. The clutch member 193 is provided with a flange 194 which cooperates with a flange 196 on the adapter 187. The adapter 187 carries an O-ring 197 seated against another flange 198 forming a part of the adapter 187. The O-ring 197 forms a liquid-tight seal with respect to the drive cable 192. The clutch member 193 is thus held in a fixed longitudinal position while still permitting rotation of the same. The adapter 187 is provided with a tapered surface 199 adapted to fit into a motor drive means. Alternatively, the clutch member 193 can be adapted for manual rotation.

The drive cable 192 has its distal extremity secured to a rotating member 203 which is provided with an inclined reflective surface 204 which serves as a reflector for reflecting ultrasonic energy generated by the transducer 182 in a transverse direction relative to the longitudinal axis of the housing 27. The angle of inclination of surface 204 may vary, typically between 45° and 85° to provide for forward viewing as described above, depending on the sweep geometry desired. As illustrated, the torque cable 192 is unable to axially translate within the lumen 191. Thus, the reflective surface 204 on rotating member 203 remains in a fixed longitudinal position relative to the housing 27 and cannot be advanced or retracted with respect to the ultrasonic transducer 182. The reflective surface 204 can, of course, be axially translated within a blood vessel by movement of the catheter 180 as a whole. Also, the catheter 180 could be modified to permit axial translation of the rotating member 203 within the housing 27 (in a manner similar to the previous catheter embodiments), but generally this will be unnecessary.

The large lumen 191 in flexible elongate tubular element 186 is in communication with a side arm port 206 which forms a part of the two-arm adapter 187. The housing 27 should be formed of a material which causes minimal attenuation of the ultrasonic signal which is transmitted and received by transducer 182. Suitable materials include polyethylene, silicone rubber, polyvinyl chloride, polyurethanes, polyesters, natural rubbers, and the like. Alternatively, the housing may be formed of acoustically opaque materials if a cutout 207 (shown by the dashed lines) is provided through which the ultrasonic energy can pass.

The operation of the catheter apparatus 180 shown in FIG. 11 is very similar to that hereinbefore described with the exception that the cutting operation is omitted. With this catheter apparatus, the device can be inserted in the same manner as with respect to the other devices hereinbefore described. When the device is in the desired location, as for example, in the stenosis, the stenosis can be imaged ultrasonically by causing the rotating member 203 to be rotated with respect to the crystal 182 to cause ultrasonic energy to be directed upwardly and outwardly through the housing 181 to impinge upon the sidewalls of the vessel in which the catheter apparatus 180 is positioned. If a different longitudinal position is desired to be scanned, the entire catheter apparatus 181 can be shifted longitudinally in the vessel to the desired location. After the ultrasonic imaging has been completed, the catheter apparatus 180 can be removed and other operations performed if desired with other instruments.

It should be appreciated that if desired, another embodiment of catheter apparatus used solely for imaging can be provided by mounting the crystal at the end of the torque cable as illustrated in FIG. 8 so that the crystal is rotated about an axis parallel to the longitudinal axis of the housing.

From the foregoing, it can be seen that a two-dimensional ultrasound image is generated by rotating a crystal or a mirror which is located at the tip of the catheter. Good resolution is obtained because of the relatively high frequency, i.e., 5 to 50 megahertz, that is used. The image which is created is generally perpendicular to the longitudinal axis of the catheter, but may also be in a forward conical pattern, depending on the precise geometry of the transducer and/or mirror. The motor or manual drive means which is utilized for rotating the transducer is external to the patient. Rotation of the transducer is made possible because of the electrical connection made with the brush contacts. The use of the balloon stabilizes the housing so that the cutting operation can be readily accomplished.

The apparatus and system of the present invention makes it possible to obtain images in very small vessels and has made it possible to accomplish the same by utilizing the precision driving of a very flexible cable. The catheter apparatus in addition to being capable of imaging is also capable of being steered by the flexible guidewire secured to the tip.

It is apparent from the foregoing that there has been provided a catheter apparatus, system and method which is particularly useful for intravascular two-dimensional ultrasonography and which can be utilized with many different types of operations, as for example, in performing atherectomies.

What is claimed is:

1. A catheter apparatus suitable for imaging the wall of a vessel in the vascular system of a patient, said catheter apparatus comprising:

an elongate tubular element exhibiting a size and flexibility sufficient to permit both introduction of said tubular element into the vessel and subsequent advancement of said tubular element through the vessel to the location of the vessel wall where imaging is desired, said tubular element including a proximal extremity, said tubular element also including a distal extremity, at least a portion of which is substantially transparent to ultrasonic energy;

ultrasonic energy generating means disposed within said distal extremity of said tubular element for generating ultrasonic energy and for propagating the ultrasonic energy so generated through said energy transparent portion of said distal extremity toward the wall of the vessel;

electrical circuit means carried by said tubular element and connected to said ultrasonic generating means for supplying power thereto; and drive means disposed within said tubular element and connected to said ultrasonic generating means for rotating said ultrasonic generating means such that ultrasonic energy therefrom is directed around the circumference of the vessel wall, said drive means including an elongate flexible drive cable structure which is fabricated at least in part from stainless steel, said drive cable structure also exhibiting a size and flexibility sufficient to permit both introduction of said tubular element into the vessel and subsequent advancement of said tubular element through the vessel to the location of the vessel wall where imaging is desired.

2. A catheter apparatus as set forth in claim 1, wherein said elongate drive cable structure is comprised of helically braided stainless steel wire.

3. A catheter apparatus as set forth in claim 1, wherein said ultrasonic generating means includes a reflective surface for reflecting ultrasonic energy generated by said ultrasonic generating means through said energy transparent portion of said distal extremity toward the wall of the vessel.

4. A catheter apparatus as set forth in claim 3, wherein said tubular element is characterized by a longitudinal axis and said ultrasonic generating means includes an ultrasonic transducer which propagates ultrasonic energy along said longitudinal axis of said tubular element to said reflective surface, whereupon said ultrasonic energy is reflected through said energy transparent portion of said distal extremity toward the vessel wall.

5. A catheter apparatus as set forth in claim 4, wherein said ultrasonic transducer and said reflective surface are spaced at a fixed, predetermined distance from one another along said longitudinal axis of said tubular element.

6. A catheter apparatus as set forth in claim 1, wherein said ultrasonic generating means includes an ultrasonic transducer which operates in the frequency range of 5 to 50 megahertz.

7. A catheter apparatus as set forth in claim 1, wherein said tubular element is shaped so as to permit fluid communication between said proximal and distal extremities, said proximal extremity including a port means through which fluid can be introduced to the interior of said tubular element for passage to said distal extremity.

8. A catheter apparatus as set forth in claim 1 wherein said elongate drive cable structure is comprised of a wound stainless steel wire.

9. An ultrasonic imaging system for obtaining an image of a small vessel of the human body comprising:

a flexible tubular element of diameter suitable for insertion in a small vessel of the human body, said flexible tubular element having a distal extremity and a proximal extremity, and a lumen communicating between the distal and proximal extremities, and a longitudinal axis;

an ultrasonic transducer means in the lumen of said elongate flexible tubular element near the distal extremity thereof, said transducer means capable of directing ultrasonic waves through said flexible tubular element and toward the walls of the small vessel, said transducer means also capable of receiving ultrasonic waves reflected from the vessel wall toward the transducer means, said transducer means having a diameter which closely matches the internal diameter of the distal portion of lumen of the flexible tubular element wherein the transducer means is rotated;

said ultrasonic transducer means being rotatable within the distal extremity of the flexible tubular element;

a high torque rotatable drive shaft running through the lumen of the flexible tubular element, said rotatable drive shaft having a distal tip secured to the ultrasonic transducer means and a proximal end connected to a motorized drive means, said motorized drive means being capable of rotating the drive shaft and transducer means within the flexible tubular element at high speeds;

a transmitter means coupled to said transducer means capable of sending electrical signals to said transducer means to cause said transducer means to direct ultrasonic waves through the flexible tubular element toward the vessel wall as the transducer means rotates within the flexible tubular element;

a receiver means coupled to the transducer means capable of receiving electrical signals emitted by the transducer means in response to ultrasonic waves reflected from the vessel wall toward the transducer means; and signal processing and display means for interpreting electrical signals received by the receiver means and displaying an image of the vessel wall based on a plurality of received signals.

10. The ultrasonic imaging system of claim 9 wherein the drive shaft has a diameter which closely matches the diameter of the lumen of the flexible tubular element wherein the drive shaft rotates, at least near the distal end thereof.

11. The ultrasonic imaging system of claim 9 wherein the ultrasonic transducer means comprises an ultrasonic transducer which directs ultrasonic waves through the flexible tubular element, said ultrasonic transducer mechanically coupled to the rotatable drive shaft and electrically connected to the transmitter means and receiver means, said transducer being rotated by the rotatable drive shaft while emitting a series of ultrasonic wave signals and receiving echoes of those signals reflected from the wall of the small vessel.

12. The ultrasonic imaging system of claim 9 wherein the ultrasonic transducer means is a transducer and mirror combination, said transducer emitting ultrasonic waves along the longitudinal axis of the flexible tubular member and said mirror aligned to reflect the ultrasonic waves away from the longitudinal axis and toward the wall of the small vessel.

13. An ultrasonic imaging probe for obtaining an image of a small vessel of the human body comprising:
a flexible tubular element of diameter suitable for insertion in a small vessel of the human body, said flexible tubular element having a distal extremity and a proximal extremity, and a lumen communicating between the distal and proximal extremities, said flexible tubular element being characterized by a longitudinal axis and a radial outward dimension relative to the longitudinal axis;
an ultrasonic transducer mounted in the distal portion of the lumen of the flexible elongate element, said transducer capable of directing ultrasonic waves along the longitudinal axis of the flexible elongate element; and receiving ultrasonic waves impinging the transducer along the longitudinal axis of the flexible elongate element;
an ultrasonic mirror rotatably disposed within the distal portion of the lumen of the flexible elongate element, said mirror capable of reflecting the ultrasonic waves emitted by the transducer away form the longitudinal axis so that the ultrasonic wave is reflected through the flexible tubular element and toward the wall of the small vessel, said mirror having a diameter which closely matches the internal diameter of the distal portion of the flexible tubular element wherein the mirror is rotated;
a rotatable drive shaft running through the lumen of the flexible tubular element, said rotatable drive shaft having a distal tip secured to the mirror and a proximal end connected t a motorized, said motorized drive means being capable of rotating the drive shaft and mirror within the flexible tubular element at high speeds;
a transmitter means coupled to the transducer capable of sending electrical signals to the transducer to cause the transducer to emit ultrasonic waves along the longitudinal axis of the flexible tubular element;
a receiver means coupled to the transducer capable of receiving electrical signals emitted by the transducer in response to ultrasonic waves reflected from the vessel wall toward the mirror and further reflected by the mirror toward the transducer; and
signal processing and display means for interpreting electrical signals received by the receiver means and displaying an image of the vessel wall based on a plurality of received signals.

14. The ultrasonic imaging probe of claim 13 further comprising a sealing means at the proximal extremity of said flexible tubular element to provide a liquid tight seal between the rotatable drive shaft and the flexible tubular element.

15. The ultrasonic imaging system of claim 13 wherein the drive shaft has a diameter which closely matches the diameter of the lumen of the flexible tubular element wherein the drive shaft rotates, at least near the distal end thereof.

16. The ultrasonic imaging system of claim 9 wherein the flexible tubular element is closed at its distal extremity and the portion of said flexible tubular element surrounding the transducer means is acoustically transparent.

17. The ultrasonic imaging system of claim 13 wherein the flexible tubular element is closed at its distal extremity and the portion of said flexible tubular element surrounding the mirror is acoustically transparent.

18. The ultrasonic imaging system of claim 9 further comprising a sealing means at the proximal extremity of said flexible tubular element to provide a liquid tight seal between the rotatable drive shaft and the flexible tubular element.

* * * * *